United States Patent
Burk

(10) Patent No.: US 8,158,676 B2
(45) Date of Patent: Apr. 17, 2012

(54) SUBSTITUTED CYCLOPENTANES HAVING PROSTAGLANDIN ACTIVITY

(75) Inventor: Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 538 days.

(21) Appl. No.: 12/276,491

(22) Filed: Nov. 24, 2008

(65) Prior Publication Data

US 2009/0143461 A1    Jun. 4, 2009

Related U.S. Application Data

(60) Provisional application No. 60/991,003, filed on Nov. 29, 2007.

(51) Int. Cl.
*A61K 31/381* (2006.01)
*C07D 333/38* (2006.01)
(52) U.S. Cl. .......................... 514/448; 549/71
(58) Field of Classification Search .................. 514/448; 549/71
See application file for complete search history.

(56) References Cited

U.S. PATENT DOCUMENTS

| | | |
|---|---|---|
| 4,259,516 A | 3/1981 | Sih |
| 6,090,847 A | 7/2000 | Woodward |
| 7,091,231 B2 | 8/2006 | Donde et al. |

FOREIGN PATENT DOCUMENTS

WO   WO 2006-063179   6/2006

OTHER PUBLICATIONS

'Common Glaucoma Treatments', http://www.ahaf.org/glaucoma/treatment/common/, accessed May 10, 2011.*
Richard Silverman; "Prodrugs and Drug Delivery Systems"; Organic Chemistry of Drug Design and Drug Action; 2d Edition Elsevier Academic Press: Amsterdam; pp. 496-597; 2004.
U.S. Appl. No. 11/569,369, filed Nov. 20, 2006, Old, David.
U.S. Appl. No. 60/886,013, filed Jan. 22, 2007, Old, David.
U.S. Appl. No. 11/748,168, filed May 14, 2007, Old, David.
U.S. Appl. No. 11/553,143, filed Oct. 26, 2006, Donde, Yariv.

* cited by examiner

*Primary Examiner* — Andrew D Kosar
*Assistant Examiner* — Karen Cheng
(74) *Attorney, Agent, or Firm* — Kevin J. Forrestal; John E. Wurst; Doina G. Ene

(57) ABSTRACT

Disclosed herein are compounds having a formula:

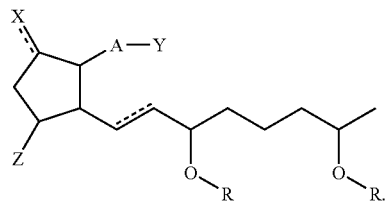

Therapeutic methods, medicaments, and compositions related thereto are also disclosed.

13 Claims, No Drawings

SUBSTITUTED CYCLOPENTANES HAVING PROSTAGLANDIN ACTIVITY

CROSS-REFERENCE TO RELATED APPLICATION

This application is based, and claims priority under 35 U.S.C. §120 to U.S. Provisional Patent Application No. 60/991,003 filed on Nov. 29, 2007, and which is incorporated herein by reference.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract. Glaucoma occurs in about 2% of all persons over the age of 40 and may be asymptotic for years before progressing to rapid loss of vision.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

In cases where surgery is not indicated, prostaglandins and prostamides have recently become the first line treatments of glaucoma. Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

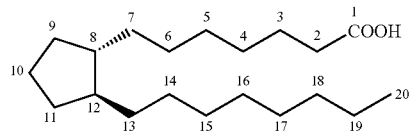

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Disclosed herein are compounds represented by the formula:

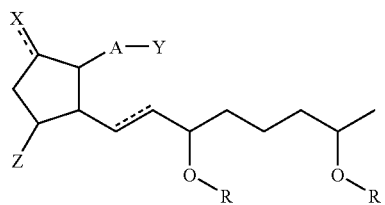

wherein a dashed line represents the presence or absence of a bond;

Y has from 0 to 14 carbon atoms and is: an organic acid functional group, or an amide or ester thereof; hydroxymethyl or an ether thereof; or a tetrazolyl functional group;

A is a 6 atom interarylated linear alkyl, ethereal, or thioethereal chain;

X is halo, =O, —OH, =S, —SH, —$CF_3$, —CN, =$CH_2$, =CHalkyl or =C(alkyl)$_2$ having from 1 to 6 carbon atoms;

Z is halo, —OH, —OR, —SH, —$CF_3$, or —CN; and each R is independently —H, $C_{1-6}$ alkyl, $C_{1-6}$ hydroxyalkyl, or $C_{1-6}$ acyl.

These compounds are useful for reducing intraocular pressure. Reduction of intraocular pressure has been shown to delay or prevent the onset of primary open angle glaucoma, and to delay or prevent further vision loss in patients with primary open angle glaucoma. Thus, these compounds are also useful for treating glaucoma. Different types of suitable dosage forms and medicaments are well known in the art, and can be readily adapted for delivery of the compounds disclosed herein. For example, the compound could be dissolved or suspended in an aqueous solution or emulsion that is buffered to an appropriate pH, and administered topically to an eye of a mammal (see U.S. Pat. No. 7,091,231).

One embodiment is a method of reducing intraocular pressure comprising administering a compound disclosed herein to a mammal in need thereof.

Another embodiment is use of a compound disclosed herein in the manufacture of a medicament for the treatment of glaucoma.

An ophthalmically acceptable liquid comprising a compound disclosed herein and an ophthalmically acceptable excipient.

For the purposes of this disclosure, "treat," "treating," or "treatment" refers to the diagnosis, cure, mitigation, treatment, or prevention of disease or other undesirable condition.

Unless otherwise indicated, reference to a compound should be construed broadly to include pharmaceutically acceptable salts, prodrugs, tautomers, alternate solid forms, non-covalent complexes, and combinations thereof, of a chemical entity of a depicted structural formula or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —$CO_2(CH_2)_2OH$,

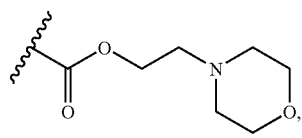

and the like. Thus, compounds represented by the formula below are examples of useful prodrugs.

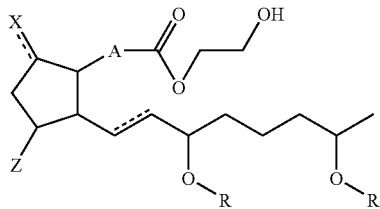

Tautomers are isomers that are in rapid equilibrium with one another. For example, tautomers may be related by transfer of a proton, hydrogen atom, or hydride ion.

Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Y is an organic acid functional group, or an amide or ester thereof; or Y is hydroxymethyl or an ether thereof; or Y is a tetrazolyl functional group. For the purposes of this disclosure, Y is limited to from 0 to 14 carbon atoms, from 0 to 5 oxygen atoms, from 0 to 2 nitrogen atoms, from 0 to 2 sulfur atoms, from 0 to 1 phosphorous, and any necessary hydrogen atoms.

An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Esters and amides of organic functional groups are carbonyl groups directly attached to a nitrogen or oxygen atom. Thus, esters of amides of carboxylic acids, sulfonic acid, and phosphonic acid functional groups are depicted below.

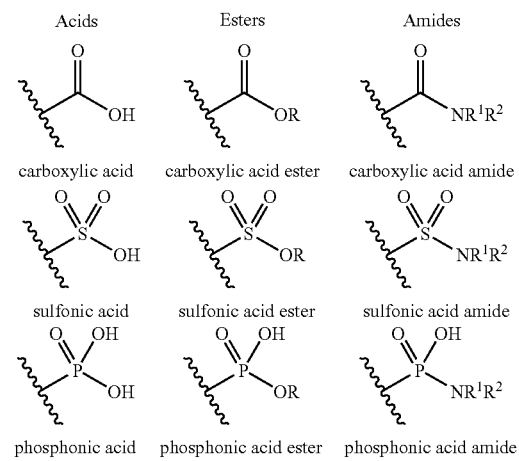

An amide may also have an —$SO_2$— moiety. For example the amide —$CONHSO_2R^3$, wherein $R^3$ is a hydrocarbyl of from 1 to 14 carbon atoms, is contemplated. R, $R^1$, $R^2$, and $R^3$ are hydrocarbyl subject to the constraint that Y may not have more than 14 carbon atoms.

Hydrocarbyl is a moiety consisting of carbon and hydrogen, including, but not limited to:

a. alkyl, which is hydrocarbyl that contains no double or triple bonds, such as:

linear alkyl, e.g. methyl, ethyl, n-propyl, n-butyl, n-pentyl, n-hexyl, etc., branched alkyl, e.g. iso-propyl, t-butyl and other branched butyl isomers, branched pentyl isomers, etc., cycloalkyl, e.g. cyclopropyl, cyclobutyl, cyclopentyl, cyclohexyl, etc., combinations of linear, branched, and/or cycloalkyl;

b. alkenyl, which is hydrocarbyl having 1 or more double bonds, including linear, branched, or cycloalkenyl;

c. alkynyl, which is hydrocarbyl having 1 or more triple bonds, including linear, branched, or cycloalkynyl;

d. unsubstituted or hydrocarbyl substituted phenyl; and e. combinations of alkyl, alkenyl, and/or alkynyl $C_{1-6}$ hydrocarbyl is hydrocarbyl having 1, 2, 3, 4, 5, or 6 carbon atoms.

$C_{1-6}$ alkyl is alkyl having 1, 2, 3, 4, 5, or 6, carbon atoms such as methyl, ethyl, propyl isomers, butyl isomers, pentyl isomer, and hexyl isomers, etc.

An unsubstituted tetrazolyl functional group has two tautomeric forms, which can rapidly interconvert in aqueous or biological media, and are thus equivalent to one another. These tautomers are shown below.

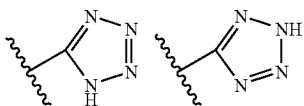

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{14}$ are considered to be within the scope of the term "tetrazolyl."

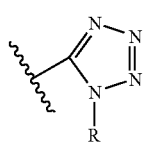

In one embodiment, Y is —$CO_2R^4$, —$CONR^5R^6$, —CON($CH_2CH_2OH)_2$, —$CONH(CH_2CH_2OH)$, —$CH_2OH$, —$P(O)(OH)_2$, —$CONHSO_2R^4$, —$SO_2NR^5R^6$,

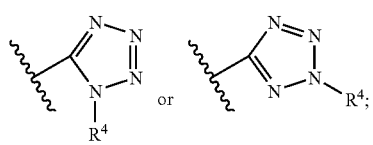

wherein $R^4$, $R^5$ and $R^6$ are independently H, $C_1$-$C_6$ alkyl, $C_{1-6}$ hydroxyalkyl, unsubstituted phenyl, or unsubstituted biphenyl, provided that Y has no more than 14 carbon atoms.

A is a 6 atom interarylated linear alkyl, ethereal, or thioethereal chain. In other words, A consists of one or two linear alkyl, linear ethereal, or linear thioethereal fragments (L) and an interarylene moiety (Ar) forming a structure -L-Ar-L-, —Ar-L-, or -L-Ar—. The atoms of the one or two L groups and 2, 3, or 4 atoms from Ar, form a 6 atom chain connecting the substituted cyclopentyl of the structure with Y. Thus, A may have one of the basic structures below, wherein:

a. the linear portions (L) may have —O— or —S— in place of one or more carbon atoms;
b. the rings may be substituted;
c. the rings may have one or more nitrogen atoms in place of a CH; and
d. Q is —S—, —O—, or —NH—.

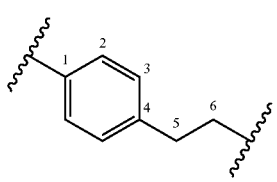

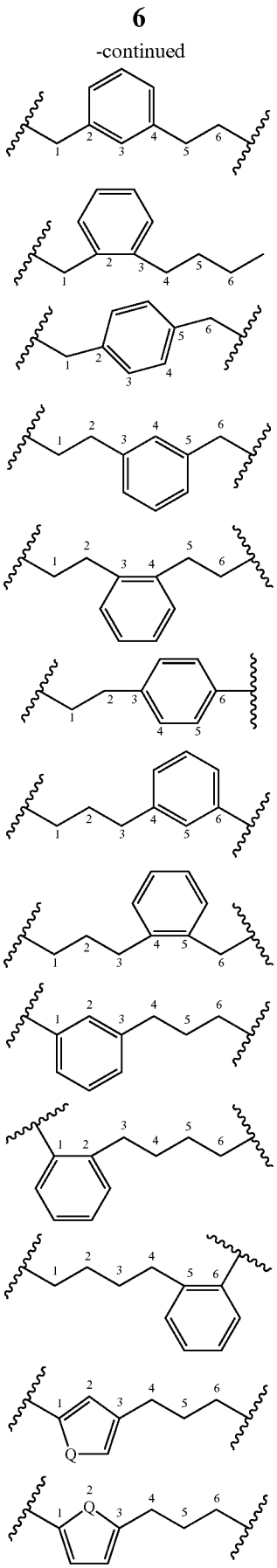

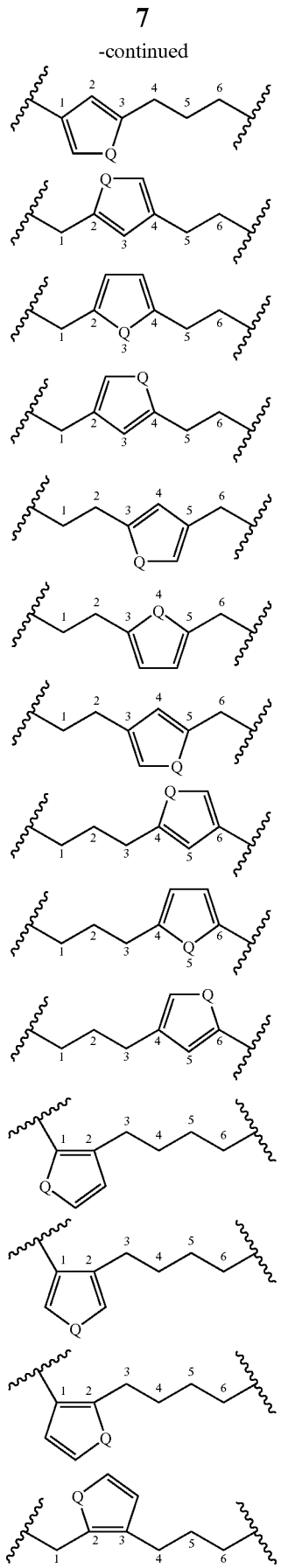
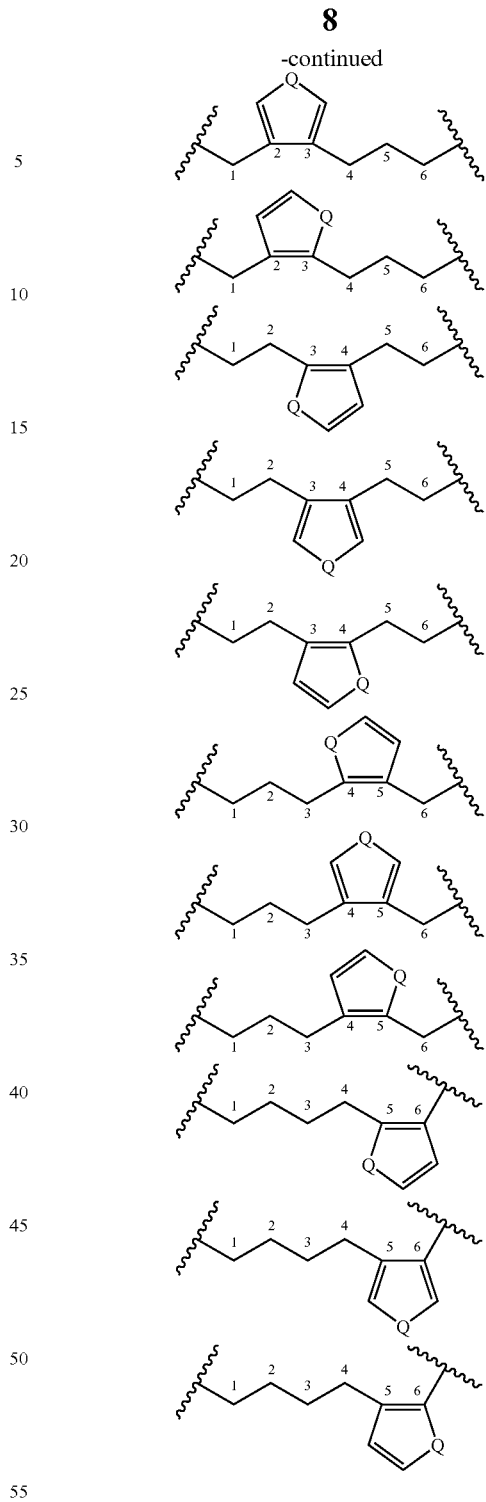

Thus, since Q is —S—, —O—, or —NH—, and the rings may have one or more nitrogen atoms in place of a CH, the ring may be, for example, pyridinyl, pyrazinyl, imidazole, thiazole, oxazole, and the like, both substituted and unsubstituted.

A linear ethereal fragment is —O-alkyl, -alkyl-O—, -alkyl-O-alkyl- or —O—CH$_2$CH$_2$—O—, where alkyl is linear.

A linear thioethereal fragment is —S-alkyl, -alkyl-S—, -alkyl-5-alkyl- or —S—CH$_2$CH$_2$—S—, where alkyl is linear.

Interarylene is aryl which connects two other parts of the molecule, i.e. L- and -L, L- and —Y, or the cyclopentyl and -L. The interarylene moiety may have substituents in addition to the 2 connecting it to the rest of the molecule. There may be as many of these substituents as the ring will bear, and if they are present they are selected from alkyl, alkoxy, acyl, acyloxy, —S-alkyl, or amino (i.e. —NH$_2$, —NHalkyl, —N(alkyl)$_2$) having from 1-4 carbon atoms, halo (—F, —Cl, —Br, —I), —CN, or —CO$_2$H.

X is halo, =O, —OH, =S, —SH, —CF$_3$, —CN, =CH$_2$, =CHalkyl or =C(alkyl)$_2$ having from 1 to 6 carbon atoms. The alkyl moieties of =C(alkyl)$_2$ are independent, i.e. they may be the same or different. Thus, for example, X may be one of the groups depicted below.

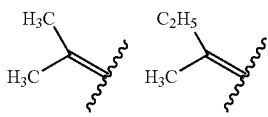

In one embodiment X is halo.
In another embodiment X is —F.
In another embodiment X is —Cl.
In another embodiment X is —Br.
In another embodiment X is —I.
In another embodiment, X is =O. For example, the compound may have a structure shown below.

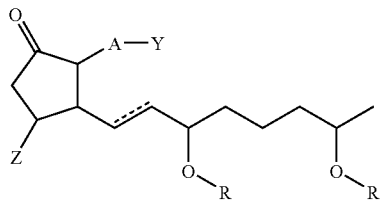

In another embodiment X is —OH.
In another embodiment X is =S.
In another embodiment X is —SH.
In another embodiment X is —CF$_3$.
In another embodiment X is —CN.
In another embodiment X is =CH$_2$.
In another embodiment X is =CHalkyl.
In another embodiment X is =C(alkyl)$_2$.
In one embodiment Z is halo.
In another embodiment Z is —F.
In another embodiment Z is —Cl.
In another embodiment Z is —Br.
In another embodiment Z is —I.
In another embodiment Z is —OH.
In another embodiment Z is —OR.
In another embodiment Z is —SH.
In another embodiment Z is —CF$_3$.
In another embodiment Z is —CN.
Each R is independently —H, C$_{1-6}$ alkyl, C$_{1-6}$ hydroxyalkyl, or C$_{1-6}$ acyl.

Hydroxyalkyl is -alkyl-OH, C$_{1-6}$ hydroxyalkyl is hydroxyalkyl having from 1-6 carbon atoms. Examples include hydroxymethyl, hydroxyethyl, etc.

Acyl is

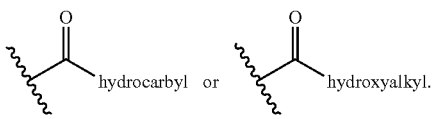

C$_{1-6}$ acyl is acyl having from 1 to 6 carbon atoms.

One embodiment is a compound represented by the formula:

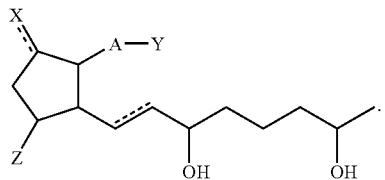

Another embodiment is a compound represented by the formula:

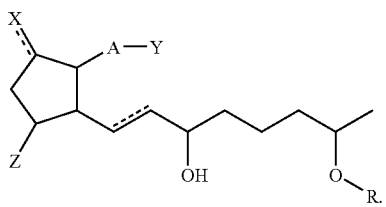

In another embodiment, R is C$_{1-6}$ alkyl in the structure above.

In another embodiment, R is C$_{1-6}$ hydroxyalkyl in the structure above.

In another embodiment, R is C$_{1-6}$ acyl in the structure above.

Another embodiment is a compound represented by the formula:

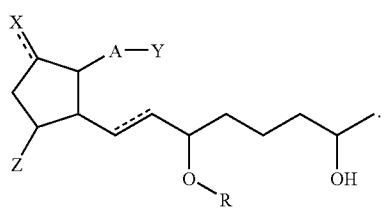

In another embodiment, R is C$_{1-6}$ alkyl in the structure above.

In another embodiment, R is C$_{1-6}$ hydroxyalkyl in the structure above.

In another embodiment, R is C$_{1-6}$ acyl in the structure above.

Another embodiment is a compound represented by the formula:

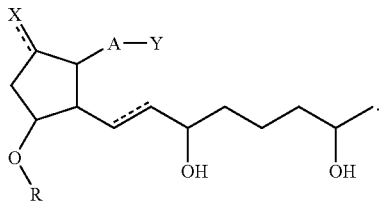

In another embodiment, R is $C_{1-6}$ alkyl in the structure above.

In another embodiment, R is $C_{1-6}$ hydroxyalkyl in the structure above.

In another embodiment, R is $C_{1-6}$ acyl in the structure above.

Another embodiment is a compound represented by the formula:

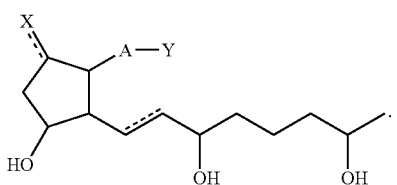

Hypothetical examples of useful compounds are depicted below.

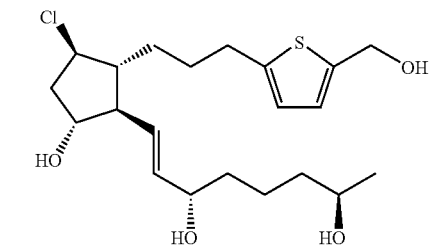

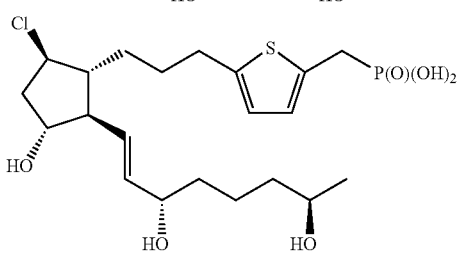

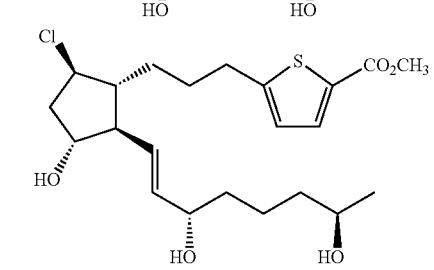

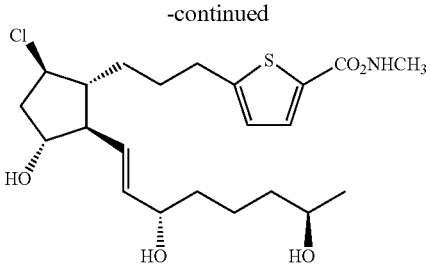

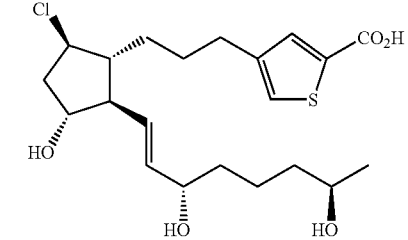

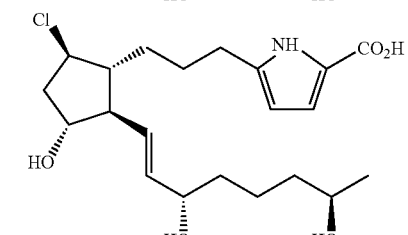

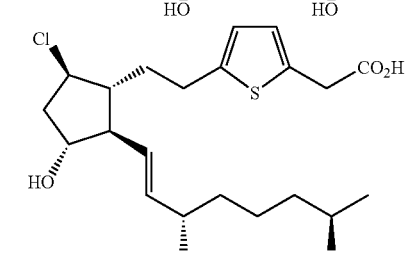

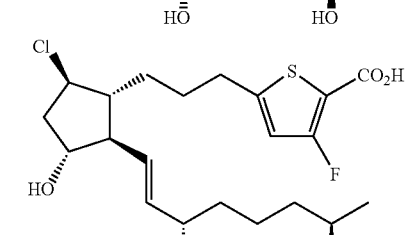

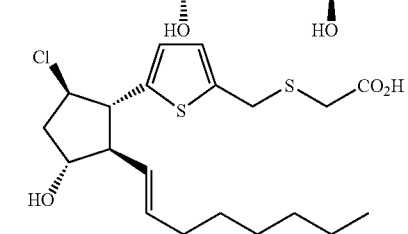

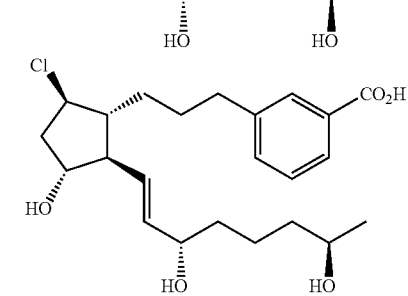

-continued
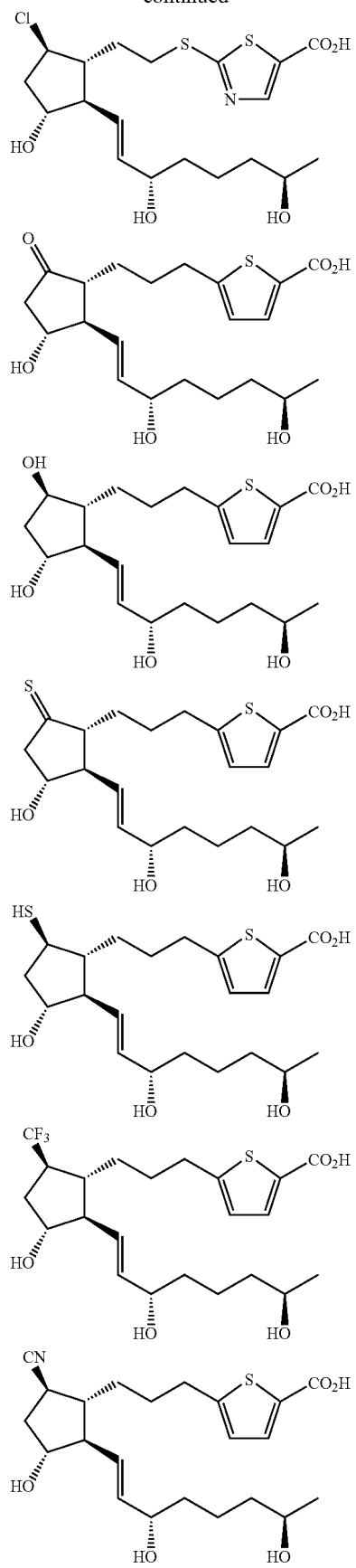
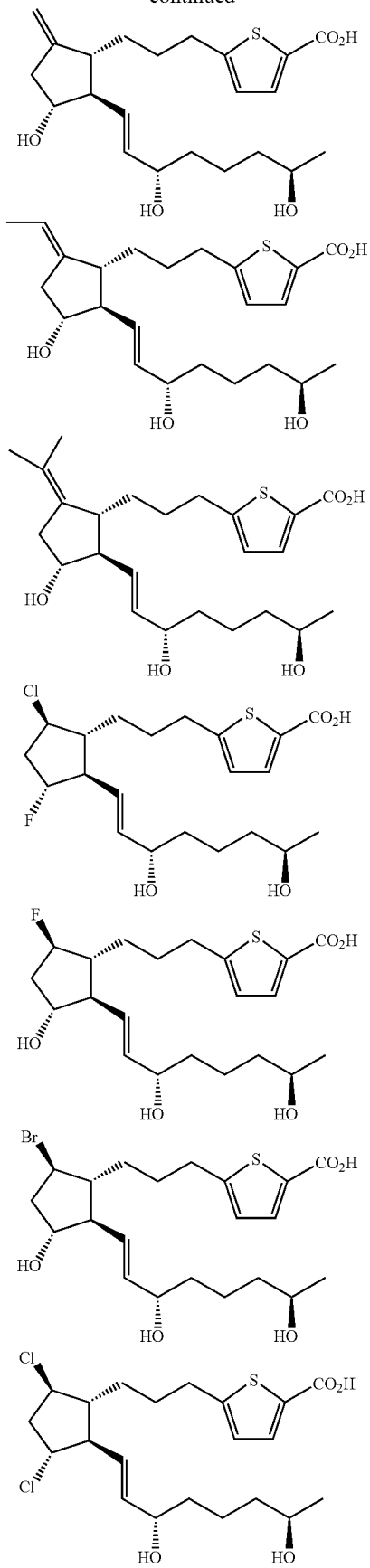

-continued

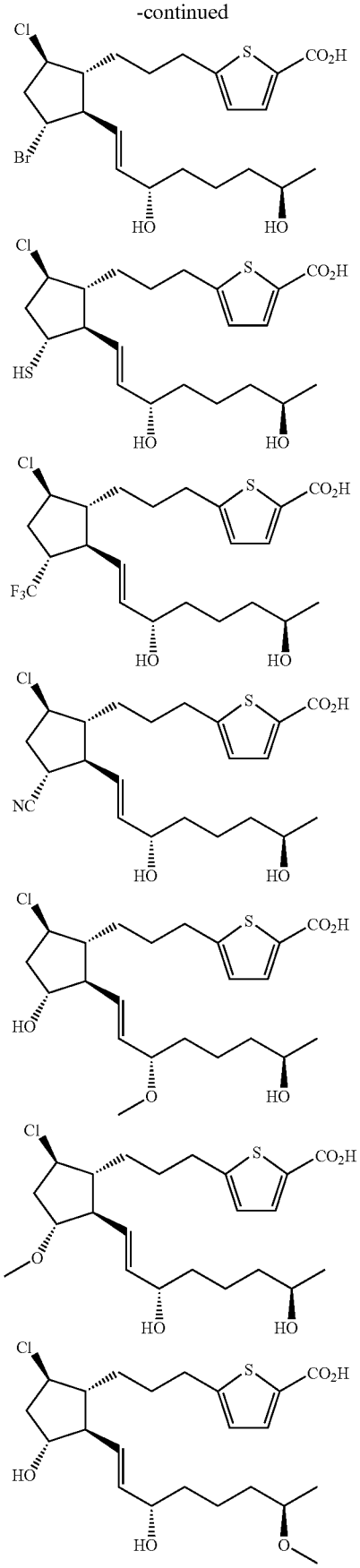

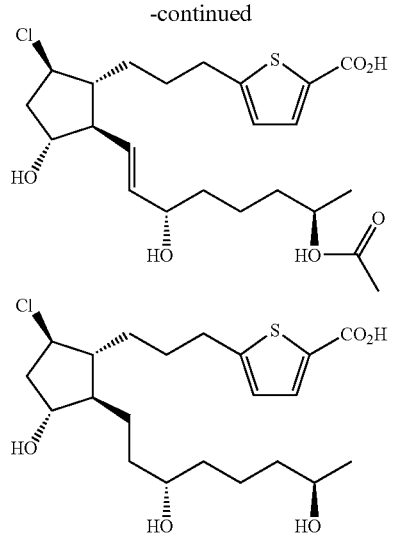

Another embodiment is a compound represented by the formula:

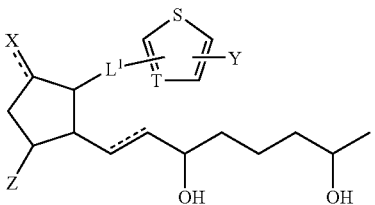

wherein $L^1$ is —(CH$_2$)$_3$—, —O(CH$_2$)$_2$—, —CH$_2$OCH$_2$—, —(CH$_2$)$_2$O—;

T is =CH— or =N—;

provided that $L^1$ and Y have a 1,3 relationship to one another.

A 1,3 relationship between L1 and Y means that the two groups are bonded to two ring carbon atoms having one ring atom between them. For example, meta substituents on phenyl have a 1, 3 relationship. The structure depicted in the embodiment below also has a 1,3-relationship between $L^1$ and Y, where the S is the one ring atom between the two carbons attached to $L^1$ and Y.

Another embodiment is a compound represented by the formula:

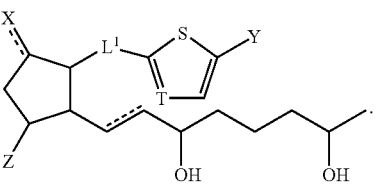

Another embodiment is a compound represented by the structure above wherein X is F, Cl, =O, or OH.

Another embodiment is a compound represented by the structure above wherein Z is OH.

Another embodiment is a compound represented by the structure above wherein Y is —CO$_2$H or an ester or amide thereof.

Another embodiment is a compound represented by the formula:

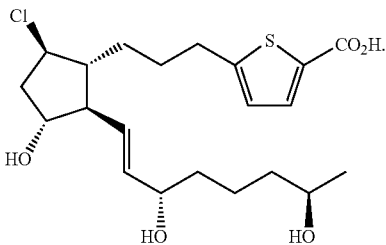

Another embodiment is a compound represented by the formula:

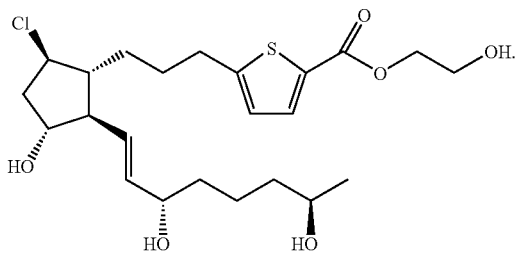

SYNTHETIC METHODS

While there are many ways to prepare the compounds disclosed herein, useful compounds may be obtained by using or adapting the following exemplary procedures.

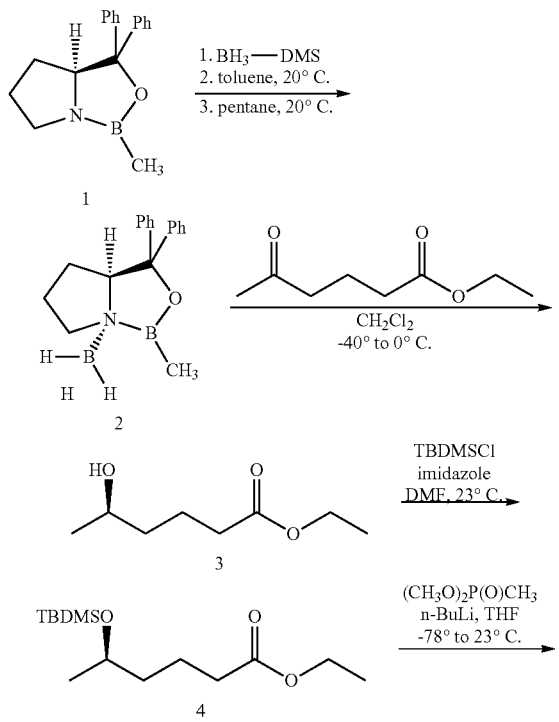

Scheme 1

-continued

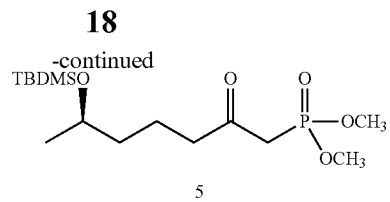

5

(S)-Methyl CBS-borane Reagent (2)

A 250 mL, 2 neck Schlenk flask was equipped with a magnetic stirbar, a $N_2$ inlet, and charged with 75 mL of (S)-methyloxazaborolidine 1 in toluene (1.0 M) at 20° C. Approximately half the volume of toluene was evaporated under vacuum with mild warming to yield about 40 mL of 2 M oxazaborolidine. Borane-dimethyl sulfide complex (10 mL, 10 M, neat) was added in one portion with rapid stirring and the resulting solution was stirred for 30 min at 20° C. Pentane (200 mL) was then added via cannula to precipitate the product (after 15 min of stirring), followed by filtration under $N_2$ and the solids were washed with 2 additional 200 mL portions of pentane. The solids were dried under a stream of nitrogen to a constant weight, affording 19.4 g (88% yield) of borane complex 2 as a white solid. The purity was estimated >90% by NMR analysis $^1$H NMR (CDCl$_3$): 0.73 (s, 3H), 1.29 (m, 2H), 1.57 (m, 2H), 1.90 (m, 2H), 3.18 (dt, 1H), 3.37 (m, 1H), 4.61 (t, 1H), 7.2-7.6 (m, 10H).

The corresponding (R)-Methyl CBS-borane reagent was prepared in the same manner starting with the (R)-methyloxazaborolidine.

Ethyl 5(R)-hydroxyhexanoate (3)

A 250 mL, round bottom flask was equipped with a magnetic stirrer, a $N_2$ inlet, a type-J teflon covered thermocouple, and charged with 6 g of (S)-methyl-CBS-borane complex 2 (20.6 mmol) dissolved in 40 mL of dichloromethane (DCM). The solution was cooled to −40° C. before ethyl 4-acetylbutyrate (3 g, 18.9 mmol) in 5 mL of DCM was added dropwise at a rate which kept the internal temperature below −20° C. At the end of addition, the dry ice/isopropanol cooling bath was substituted with an ice bath maintaining the internal reaction temperature at 0° C. for an additional hour. G.C. analysis showed less than 5% starting ketone. The reaction was worked up after 2 h at 0° C. by cautious addition of saturated aqueous ammonium chloride (100 mL). The mixture was transferred to a separatory funnel and extracted with ethyl acetate (2×100 mL). The separated combined organic extracts were washed with brine and dried over anhydrous sodium sulfate, filtered, and concentrated in vacuo to yield 7 g of crude products. Flash column chromatography (FCC) on 120 g of flash grade silica gel eluting with 20% EtOAc-hexanes yielded 1.94 g (65%) of alcohol 3 as an oil. G.C. analysis indicated a purity of 97.4A %. $^1$H NMR (CDCl$_3$): 1.20 (d, J=3 Hz, 3H), 1.26 (t, J=7.2 Hz, 3H), 1.47 (m, 2H), 1.71 (m, 3H), 2.34 (t, J=7.5 Hz, 2H), 3.89 (m, 1H), 4.13 (q, J=7.2 Hz, 2H).

Ethyl 5(R)-t-butyldimethylsilyloxyhexanoate (4)

A solution of ethyl 5(R)-hydroxyhexanoate 3 (1.80 g, 11.24 mmol), imidazole (2.3 g, 33.8 mmol), and t-butyldimethylsilyl chloride (2.54 g, 16.85 mmol) in 30 mL of DMF was stirred at 23° C. overnight (19 h). The solvent (DMF) was then removed in vacuo and aqueous saturated sodium bicarbonate (100 mL) was added followed by ethyl acetate (100 mL). The layers were separated and the aqueous layer was re-extracted with 100 mL of EtOAc. The combined organic layers were washed with water, brine, and dried over anhydrous sodium sulfate. Flash column chromatographic purification on 30 g of silica gel yielded 2.71 g (88%) of TBDMS-ether 4 (G.C. purity of 99+A %); $^1$H NMR (CDCl$_3$): 0.04 (s, 6H), 0.91 (s, 9H), 1.18 (d, J=6 Hz, 3H), 1.25 (t, J=7.2 Hz, 3H), 1.42 (m, 2H), 1.65 (m, 2H), 2.39 (t, J=7.5 Hz, 2H), 3.79 (m, J=6 Hz, 1H), 4.12 (q, J=7.2 Hz, 2H).

Dimethyl 6(R)-6-{[t-butyl(dimethyl)silyl]oxy}-2-oxoheptylphosphonate (5)

To a solution of dimethyl methylphosphonate (2.12 mL, 19.6 mmol) in 25 mL of THF at −78° C. was added butyllithium in hexanes (13.5 mL of a 1.6 M solution in hexanes, 21.6 mmol). The mixture was stirred under nitrogen at this temperature for 30 minutes before a solution of ethyl 5(R)-t-butyldimethylsilyloxyhexanoate 4 (2.7 g, 9.8 mmol) in 8 mL of THF was added dropwise. The mixture was stirred overnight during which the temperature was allowed to warm to room temperature of 25° C. The reaction was sampled by TLC after 18 h (R$_f$ of product was 0.6 in ethyl acetate) and worked up by addition of saturated aqueous ammonium chloride (100 mL). The product was extracted from the aqueous layer with ethyl acetate and washed with brine. The combined ethyl acetate extracts were dried over anhydrous sodium sulfate and concentrated to yield 3.7 g of crude products. Flash column chromatographic purification on 120 g of silica gel eluted with 3:1 ethyl acetate:hexanes yielded 2.65 g (76% yield) of purified phosphonate 5 as a clear oil; $^1$H NMR (CDCl$_3$): 0.04 (s, 6H), 0.88 (s, 9H), 1.11 (d, J=6 Hz, 3H), 1.30-1.75 (m, 4H), 2.62 (t, J=7.2 Hz, 2H), 3.08 (d, J=22.5 Hz, 2H), 3.77 (s, 3H), 3.80 (s, 3H).

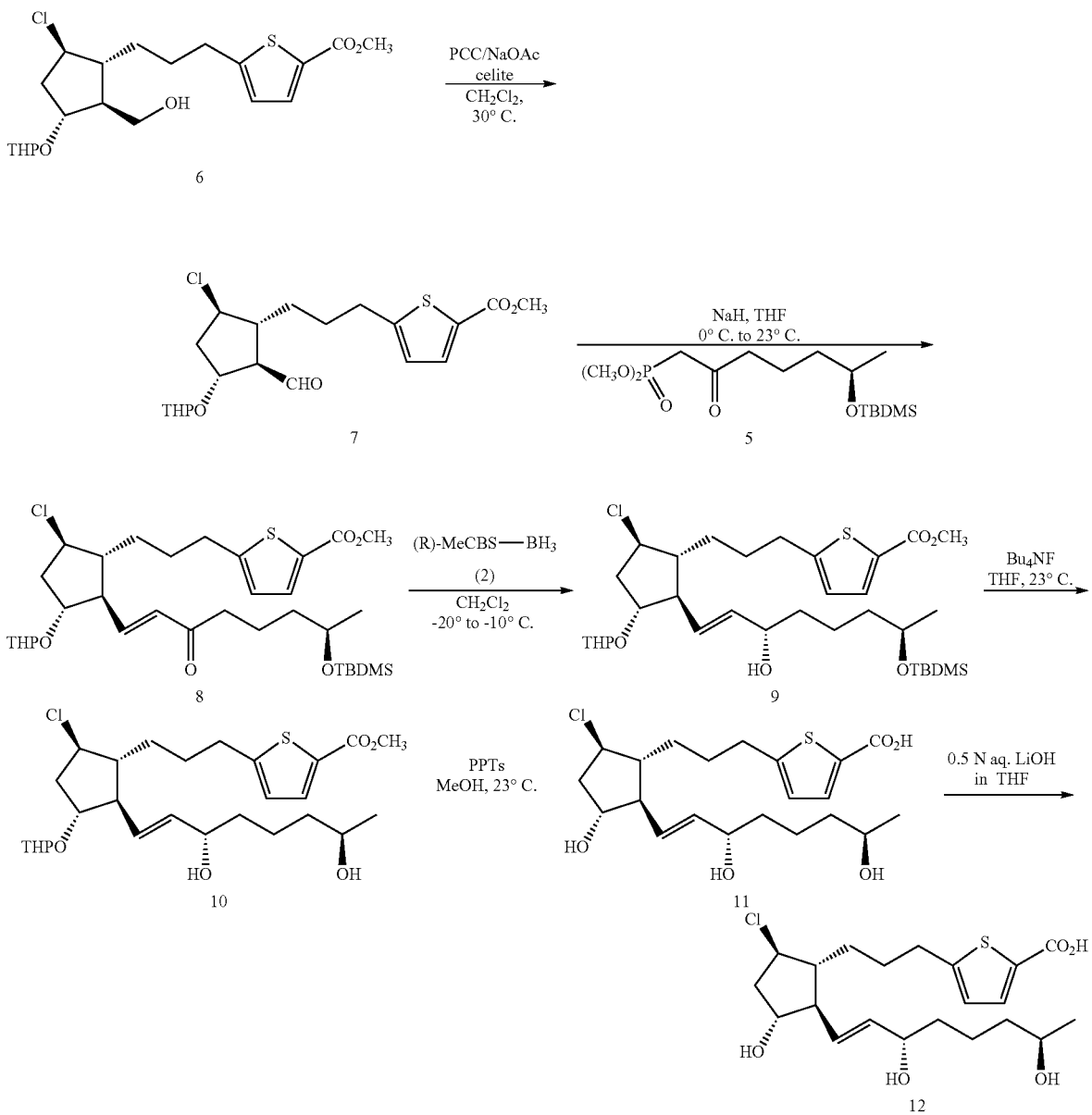

Methyl 5-(3-((1R,2R,3R,5R)-5-chloro-2-formyl-3-(tetrahydro-2H-pyran-2-yloxy)cyclopentyl)propyl)thiophene-2-carboxylate (7)

A solution of 330 mg of alcohol 6 (0.79 mmol) in 2 mL of dichloromethane was added via pipette to a mixture of PCC (400 mg, 1.86 mmol), sodium acetate (150 mg, 1.83 mmol), and Celite (600 mg) in 5 mL of DCM. The pipette was rinsed with an additional 3 mL of DCM to complete the transfer. The mixture was stirred sealed in a 30° C. water bath for 1.5 h. The mixture was worked up by filtration through 10 g of silica gel and washed with 100 mL of 1:1 EA:hexanes. The filtrate was concentrated in vacuo to yield the crude aldehyde as an oil. The crude product was purified by preparative thin layer chromatography (2×2 mm thick plates, eluted in 1:1 hexanes: EtOAc), to yield 238 mg (72%) of aldehyde 7; $^1$H NMR (CDCl$_3$): 1.53 (br m, 6H), 1.6-1.85 (m, 5H), 2.05-2.72 (m, 4H), 2.87 (t, J=6.3 Hz, 2H), 3.49 (m, 1H), 3.80 (m, 1H), 3.86 (s, 3H), 4.05 (m, 1H), 4.55 (m, 1H), 4.63 (m, 1H), 6.79 (d, J=3.9 Hz, 1H), 7.63 (d, J=3.9 Hz, 1H), 9.78 (dd, J=10.8 and 1.8 Hz, 1H).

Methyl 5-(3-((1R,2R,3R,5R)-2-((R,E)-7-(tert-butyldimethylsilyloxy)-3-oxooct-1-enyl)-5-chloro-3-(tetrahydro-2H-pyran-2-yloxy)cyclopentyl)propyl)thiophene-2-carboxylate (8)

To a suspension of 54 mg of sodium hydride (60% oil dispersion, 1.35 mmol) in 1 ml of THF at 0° C. was added a solution of dimethyl (6R)-6-{[tert-butyl(dimethyl)silyl]oxy}-2-oxoheptylphosphonate 5 (552 mg, 1.57 mmol) in 1 mL THF. The mixture was stirred at 0° C. for 30 min before a solution of aldehyde 7 (460 mg, 1.1 mmol) in 1 ml of THF was added dropwise. The syringe containing the aldehyde was rinsed with 2 mL of THF to complete the addition and the mixture was stirred at 25° C. for 2.5 h. The reaction was worked up with addition of saturated aqueous ammonium chloride (50 mL) and the aqueous layer was extracted with ethyl acetate (2×75 mL). The ethyl acetate layers were combined and washed with brine, dried over 30 g of anhydrous sodium sulfate, filtered and concentrated in vacuo to yield 920 mg of crude products. Flash chromatographic purification using a 24 g silica gel cartridge eluted with 10% EtOAc-hexanes yielded 430 mg (60%) of purified enone 8; $^1$H NMR (CDCl$_3$): 0.05 (s, 6H), 0.88 (s, 9H), 1.12 (d, J=6.3 Hz, 3H), 1.37-1.80 (m, 14H), 2.00 (m, 1H), 2.20 (m, 1H), 2.34 (m, 1H), 2.53 (m, 1H), 2.54 (t, J=7.2 Hz, 2H), 2.83 (m, 2H), 3.45 (m, 1H), 3.80 (m, 2H), 3.86 (s, 3H), 4.02 (m, 1H), 4.17 (m, 1H), 4.57 (m, 1H), 6.15 (m, 1H), 6.77 (m, 1H), 7.62 (d, J=3.9 Hz).

Methyl 5-(3-((1R,2R,3R,5R)-2-((3S,7R,E)-7-(tert-butyldimethylsilyloxy)-3-hydroxyoct-1-enyl)-5-chloro-3-(tetrahydro-2H-pyran-2-yloxy)cyclopentyl)-propyl)thiophene-2-carboxylate (9)

A solution of enone 8 (400 mg, 0.62 mmol) in 7 mL of dichloromethane was cooled to −20° C. and stirred rapidly while solid (R)-methylCBS-borane complex 2 (290 mg, 1.0 mmol), was added in one portion. The resulting solution was stirred at −20° to −10° C. for 1 h. TLC analysis at this stage showed no starting material left and the reaction mixture was quenched with 1 mL of methanol, the cooling bath was removed and the mixture was stirred at 20° C. 30 min. The mixture was concentrated in vacuo to remove solvents and the residual products were purified by FCC on silica gel (40 g Silicycle cartridge) to yield 40 mg of (15R+S) isomers and 325 mg of (15S)-alcohol 9; $^1$H NMR (CDCl$_3$): 0.03 (s, 6H), 0.87 (s, 9H), 1.09 (d, J=6.3 Hz, 3H), 1.30-1.90 (m, 18H), 2.05-2.35 (m, 3H), 2.82 (m, 2H), 3.45 (m, 1H), 3.76 (m, 2H), 3.84 (s, 3H), 3.97 (m, 1H), 4.07 (m, 2H), 4.60 (dt, J=4.2 Hz, 11.1 Hz, 1H), 5.57 (m, 2H), 6.77 (d, J=3.9 Hz, 1H), 7.61 (d, J=3.9 Hz, 1H).

Methyl 5-(3-((1R,2R,3R,5R)-5-chloro-2-((3S,7R,E)-3,7-dihydroxyoct-1-enyl)-3-(tetrahydro-2H-pyran-2-yloxy)cyclopentyl)propyl)thiophene-2-carboxylate (10)

A solution of silyl ether 9 (325 mg, 0.51 mmol) in 1 mL of THF was stirred at 30° C. with 2 mL of 1.0M TBAF/THF in a vial for 7.5 h. TLC indicated starting material was mostly desilylated and the reaction was concentrated in vacuo. The residual crude products were taken up in 50 mL of ethyl acetate and washed sequentially with saturated aqueous ammonium chloride (50 mL), brine (50 mL), and dried over 10 g of anhydrous sodium sulfate. The mixture was filtered and concentrated in vacuo. The residual products were purified by preparative layer chromatography on 2×2 mm thick silica gel plates eluted in EtOAc (Rf=0.5). Extraction of the major band yielded 214 mg (80%) of pure diol 10 as an oil; $^1$H NMR (CDCl$_3$): 1.18 (d, J=6 Hz, 3H), 1.38-1.68 (m, 11H), 1.66-2.37 (m, 9H), 2.84 (t, J=7.2 Hz, 2H), 3.47 (m, 1H), 3.79 (m, 1H), 3.86 (s, 3H), 3.98 (p, J=7.5 Hz, 1H), 4.09 (m, 2H), 4.63 (dt, J=3, 27 Hz, 2H), 5.58 (m, 2H), 6.78 (dd, J=0.6, 3.6 Hz, 1H), 7.62 (d, J=3.6 Hz, 1H).

Methyl 5-(3-((1R,2R,3R,5R)-5-chloro-2-((3S,7R,E)-3,7-dihydroxyoct-1-enyl)-3-hydroxycyclopentyl)propyl)thiophene-2-carboxylate (11)

A 20 mL vial equipped with a magnetic stirbar was charged with 210 mg of THP-ether 10 (0.40 mmol) was dissolved in 6 mL of methanol. To this was then added 300 mg of pyridinium p-toluenesulfonate (1.20 mmol) and the mixture was stirred at 17° C. over 17 h. The reaction was sampled by TLC and worked up by concentration in vacuo to remove methanol. The residual products were taken up in ethyl acetate and filtered through a 10 g plug of silica gel, eluting the polar product away from the salts with ethyl acetate (300 mL). Concentration of the filtrate yielded 170 mg of products. Final preparative thin layer chromatographic purification yielded 161 mg (91%) of triol 11 as an oil; $^1$H NMR (CDCl$_3$): 1.18 (d, J=6.3 Hz, 3H), 1.36-1.62 (m, 8H), 1.77 (m, 3H), 1.94 (m, 2H), 2.10-2.34 (m, 5H), 2.43 (Br s, 1H), 2.83 (m, 2H), 3.50 (br s, 1H), 3.71 (br s, 1H), 3.79 (m, 1H), 3.86 (s, 3H), 3.98 (m, 1H), 4.09 (m, 1H), 5.51 (m, 2H), 6.78 (dd, J=3.9 Hz, 1H), 7.62 (d, J=3.9 Hz, 1H).

5-(3-((1R,2R,3R,5R)-5-chloro-2-((3S,7R,E)-3,7-dihydroxyoct-1-enyl)-3-hydroxycyclopentyl)propyl)thiophene-2-carboxylic Acid (12)

A solution of 76 mg of ester 11 (0.17 mmol) in 1 mL of THF was hydrolyzed with 360 uL of aqueous lithium hydroxide (0.5M, 0.18 mmol)) and 0.2 mL of methanol at 24° C. for 6 h. The mixture was acidified by addition of solid sodium hydrogen sulfate (25 mg, 0.18 mmol) and the residual water was removed in vacuo. The residual solid was extracted with ethyl acetate and the product acid was purified by PLC on a 0.5 mm thick preparative silica gel plate eluted in 10% methanol:90% ethyl acetate. Extraction of the UV-active band yielded 43 mg of free acid 12 as an oil (54% yield); $^1$H NMR (CD$_3$OD): 1.13 (d, J=6.3 Hz, 3H), 1.28-1.63 (m, 8H), 1.75-2.21 (m, 6H), 2.86

(t, J=7 Hz, 2H), 3.70 (m, 1H), 4.04 (m, 3H), 5.52 (m, 2H), 6.86 (br s, 1H), 7.58 (br s, 1H). HPLC purity was 100A %. LCMS (ESI: M$^+$-H$_2$O): 413.2.

freshly prepared solution of absolute ethanol (11.9 mL of a 1.0M solution in THF, 7.50 mmol) was added dropwise at 23° C. After 15 min a solution of (S)-(−)-1,1'-binaphthol (2.18 g,

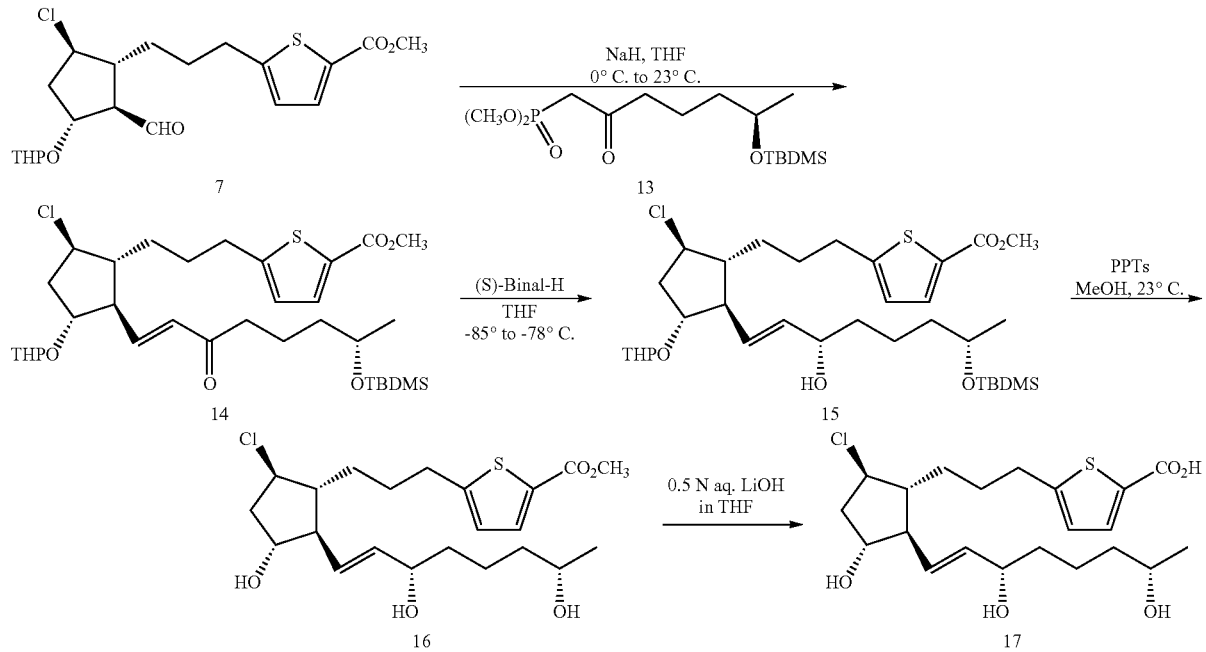

Scheme 3

Dimethyl (S)-6-(tert-butyldimethylsilyloxy)-2-oxo-heptylphosphonate (13)

Dimethyl (S)-6-(tert-butyldimethylsilyloxy)-2-oxoheptylphosphonate 13 was prepared according to the procedures described for compound 5 in Scheme 1.

Methyl 5-(3-((1R,2R,3R,5R)-2-((S,E)-7-(tert-butyldimethylsilyloxy)-3-oxooct-1-enyl)-5-chloro-3-(tetrahydro-2H-pyran-2-yloxy)cyclopentyl)propyl)thiophene-2-carboxylate (14)

To a suspension of 160.3 mg of sodium hydride (60% oil dispersion, 4.00 mmol) in 8 ml of THF at 0° C. was added a solution of dimethyl (S)-6-(tert-butyldimethylsilyl-oxy)-2-oxoheptylphosphonate 13 (1.41 g, 4.00 mmol) in 4 mL THF. The mixture was stirred at 0° C. for 30 min before a solution of aldehyde 7 (1.10 g, 2.65 mmol) in 4 ml of THF was added dropwise. The syringe containing the aldehyde was rinsed with 2 mL of THF to complete the addition and the mixture was stirred at 25° C. for 2.5 h. The reaction was worked up with addition of saturated aqueous ammonium chloride (50 mL) and the aqueous layer was extracted with ethyl acetate (2×75 mL). The ethyl acetate layers were combined and washed with brine, dried over 30 g of anhydrous sodium sulfate, filtered and concentrated in vacuo. FCC (flash column chromatography) purification (silica gel, 6:1 hex/EtOAc) provided 1.60 g (95%) of enone 14.

Methyl 5-(3-((1R,2R,3R,5R)-2-((3S,7S,E)-7-(tert-butyldimethylsilyloxy)-3-hydroxyoct-1-enyl)-5-chloro-3-(tetrahydro-2H-pyran-2-yloxy)cyclopentyl)-propyl)thiophene-2-carboxylate (15)

Lithium aluminum hydride (7.5 mL of a 1.0M solution in THF, 7.5 mmol) was added to an oven-dried 200 mL flask. A 7.62 mmol) in THF (10 mL) was added dropwise. The milky-white solution was cooled to −85° C. and a solution of the enone 14 (1.60 g, 2.50 mmol) in THF (9 mL) was added over a 5-10 min period. The reaction solution was stirred for 1 h and then warmed to −78° C. and allowed to stir an additional 3 h. The reaction was then quenched by careful addition of MeOH (3.1 mL). The reaction was then allowed to warm to room temperature and was extracted with EtOAc (2×). The combined organic portions were washed with 1N HCl, saturated aqueous NaHCO$_3$, and brine. The organic portion was then dried over anhydrous MgSO$_4$), filtered and concentrated in vacuo. FCC (silica gel, 6:1 hex/EtOAc) afforded 1.20 g (75%) of (S)-alcohol 15.

Methyl 5-(3-((1R,2R,3R,5R)-5-chloro-2-((3S,7S,E)-3,7-dihydroxyoct-1-enyl)-3-hydroxycyclopentyl)propyl)thiophene-2-carboxylate (16)

Pyridinium p-toluenesulfonate (20.4 mg, 0.081 mmol) was added to a solution of the THP-ether 15 (52 mg, 0.081 mmol) in MeOH (3 mL) at 23° C. The reaction was stirred for 24 h and then concentrated in vacuo. The residue was diluted with EtOAc and washed with 1N HCl, saturated aqueous NaHCO$_3$ and brine. The organic portion was dried over anhydrous MgSO$_4$, filtered and concentrated in vacuo. The crude product was purified by FCC (silica gel, 19:1 EtOAc/MeOH) to afford 34.9 mg (97%) of triol 11.

5-(3-((1R,2R,3R,5R)-5-chloro-2-((3S,7S,E)-3,7-dihydroxyoct-1-enyl)-3-hydroxycyclopentyl)propyl)thiophene-2-carboxylic Acid (17)

A solution of 40 mg of ester 16 (0.09 mmol) in 0.72 mL of THF was hydrolyzed with 360 uL of aqueous lithium hydroxide (0.5M, 0.18 mmol)) at 23° C. for 16 h. The mixture was acidified by addition of 1N HCl and then extracted with EtOAc (2×). The combined organic portions were washed with brine (2×), dried over anhydrous $Na_2SO_4$, filtered and concentrated in vacuo to yield 23.3 mg (60%) of the free acid 17.

Different groups for A, X, and Z may be obtained as described elsewhere. See for example, U.S. patent application Ser. No. 11/569,369, filed on Nov. 20, 2006; U.S. Provisional Patent Application Ser. No. 60/886,013, filed on Jan. 22, 2007; and U.S. patent application Ser. No. 11/748,168, filed on May 14, 2007. Other synthetic routes may also be used to reach the compounds disclosed herein.

In Vitro Testing

U.S. patent application Ser. No. 11/553,143, filed on Oct. 26, 2006, incorporated by reference herein, describes the methods used to obtain the in vitro data in Table 1 below.

TABLE 1

| AGN-# | cAMP $EC_{50}$ (nM) | $EP_2$ $Ca^{2+}$signal % $PGE_2$ | $EC_{50}$ (nM) | Binding % Inh | $EC_{50}$ (nM) | $EP_4$ $Ca^{2+}$signal % $PGE_2$ | $EC_{50}$ (nM) | Binding % Inh | $EC_{50}$ (nM) | $EP_1$ $EC_{50}$ (nM) | $EP_3$ $EC_{50}$ (nM) | $DP_2$ $EC_{50}$ (nM) | TP $EC_{50}$ (nM) |
|---|---|---|---|---|---|---|---|---|---|---|---|---|---|
| 191286 | 0.7 | 100 | 28 | 92 | 530 | 100 | 192 | 75 | 1507 | 308 | 11 | | 3010 |
| 191287 | 0.9 | 100 | 34 | 87 | 487 | 102 | 193 | 75 | 1670 | 2756 | 21 | | 5270 |
| 217510 | 0.06 | 106 | 7.4 | 99 | 66 | 121 | 145 | 64 | 2347 | 724 | 499 | | 6792 |
| 217613 | 0.03 | 107 | 4 | 99 | 25 | 107 | 46 | 81 | 885 | 13 | 6 | 1816 | 178 |
| 217712 | 1.47 | 100 | 109 | 78 | 1219 | 99 | 727 | 29 | | | | | |

TABLE 1-continued

| AGN-# | cAMP EC50 (nM) | EP2 Ca²⁺signal % PGE2 | EP2 Ca²⁺signal EC50 (nM) | EP2 Binding % Inh | EP2 Binding EC50 (nM) | EP4 Ca²⁺signal % PGE2 | EP4 Ca²⁺signal EC50 (nM) | EP4 Binding % Inh | EP4 Binding EC50 (nM) | EP1 EC50 (nM) | EP3 EC50 (nM) | DP2 EC50 (nM) | TP EC50 (nM) |
|---|---|---|---|---|---|---|---|---|---|---|---|---|---|
| 219309 | 25 | 63 | 4022 | 68 | 3306 | | | 9 | >10⁴ | | | | |
| 219310 | 3 | 77 | 281 | 90 | 171 | | | 6 | >10⁴ | | | | |
| 221568 | 1.4 | 91 | 20 | 91 | 381 | 120 | 35 | 98 | 1279 | | | | |

What is claimed is:

1. A compound represented by the formula:

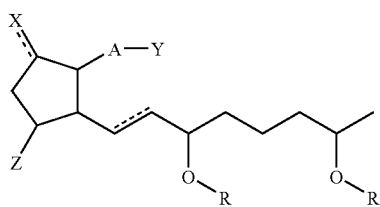

wherein a dashed line represents the presence or absence of a bond;

Y has from 0 to 14 carbon atoms and is: an organic acid functional group, or an amide or ester thereof; hydroxymethyl or an ether thereof; or a tetrazolyl functional group;

A is a 6 atom interarylated linear alkyl;

X is halo, =O, —OH, =S, —SH, —CF₃, —CN, =CH₂, =CHalkyl or =C(alkyl)₂ having from 1 to 6 carbon atoms;

Z is halo, —OH, —OR, —SH, —CF₃, or —CN; and each R is independently —H, $C_{1-6}$ alkyl, $C_{1-6}$ hydroxyalkyl, or $C_{1-6}$ acyl.

2. The compound of claim 1 wherein Y is —CO₂R⁴, —CONR⁵R⁶, —CON(CH₂CH₂OH)₂, —CONH(CH₂CH₂OH), —CH₂OH, —P(O)(OH)₂, —CONHSO₂R⁴, —SO₂NR⁵R⁶,

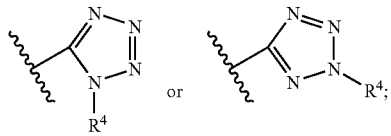

wherein R⁴, R⁵ and R⁶ are independently H, $C_1$-$C_6$ alkyl, $C_{1-6}$ hydroxyalkyl, unsubstituted phenyl, or unsubstituted biphenyl, provided that Y has no more than 14 carbon atoms.

3. The compound of claim 2 represented by the formula:

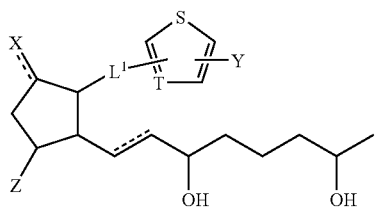

wherein $L^1$ is —(CH$_3$)$_3$

T is =CH— or =N—;

provided that $L^1$ and Y have a 1,3 relationship to one another.

4. The compound of claim 3 represented by the formula:

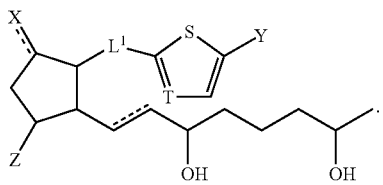

5. The compound of claim 4 wherein Y is —CO$_2$H or an ester or amide thereof.

6. The compound of claim 4 wherein X is F, Cl, =O, or OH.

7. The compound of claim 6 wherein Z is OH.

8. The compound of claim 7 represented by the formula:

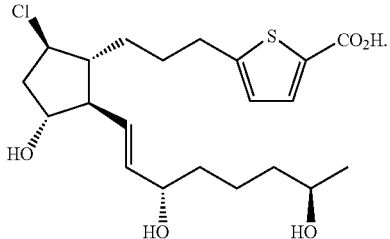

9. A compound represented by the formula:

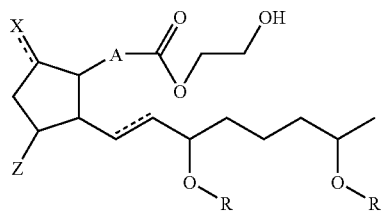

wherein a dashed line represents the presence or absence of a bond;

A is a 6 atom interarylated linear alkyl;

X is halo, =O, —OH, =S, —SH, —CF$_3$, —CN, =CH$_2$, =CHalkyl or =C(alkyl)$_2$ having from 1 to 6 carbon atoms;

Z is halo, —OH, —OR, —SH, —CF$_3$, or —CN; and each R is independently —H, C$_{1-6}$ alkyl, C$_{1-6}$ hydroxyalkyl, or C$_{1-6}$ acyl.

10. The compound of claim 9 represented by the formula:

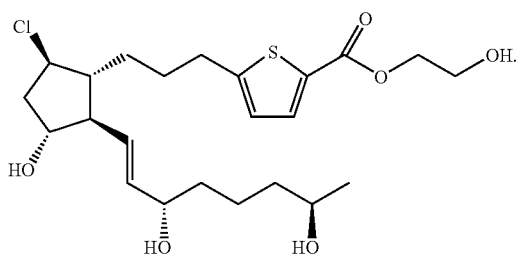

11. The compound of claim 9 represented by the formula

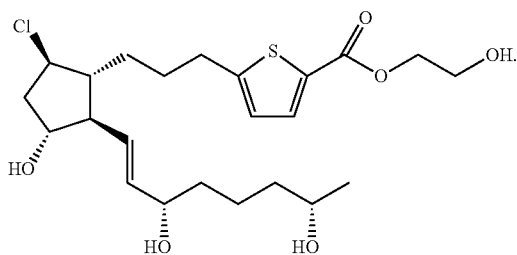

12. An ophthalmically acceptable liquid comprising a compound according to claim 1 and an ophthalmically acceptable excipient.

13. A method of reducing intraocular pressure comprising administering a compound according to claim 1 to a mammal in need thereof.

* * * * *